United States Patent
Levinson et al.

(10) Patent No.: US 6,508,829 B1
(45) Date of Patent: Jan. 21, 2003

(54) SHAPED SUTURE CLIP, APPLIANCE AND METHOD THEREFOR

(76) Inventors: Melvin E. Levinson, 12700 SW. 64th Ct., Miami, FL (US) 33156; Russell C. Flugrad, 417 Hart St., Southington, CT (US) 06489; Michael J. Drost, 21 Orchard Ter., East Hartford, CT (US) 06108; Edward W. Kalat, 310 Annelise Ave., Southington, CT (US) 06489

( * ) Notice: Subject to any disclaimer, the term of this patent is extended or adjusted under 35 U.S.C. 154(b) by 76 days.

(21) Appl. No.: 09/651,074

(22) Filed: Aug. 30, 2000

Related U.S. Application Data

(62) Division of application No. 09/330,439, filed on Jun. 11, 1999, now Pat. No. 6,165,204.

(51) Int. Cl.[7] .............................................. A61B 17/04
(52) U.S. Cl. ........................ 606/232; 606/142; 606/157
(58) Field of Search ................................. 606/140, 141, 606/142, 157, 232

(56) References Cited

U.S. PATENT DOCUMENTS

| | | | |
|---|---|---|---|
| 3,665,924 A | 5/1972 | Noiles et al. ................ | 128/305 |
| 3,675,688 A | 7/1972 | Bryan et al. .............. | 140/83 D |
| 3,735,762 A | 5/1973 | Bryan et al. ................. | 128/305 |
| 3,740,994 A | 6/1973 | De Carlo, Jr. . .............. | 72/407 |
| 3,777,538 A | 12/1973 | Weatherly et al. ............ | 72/410 |
| 3,819,100 A | 6/1974 | Noiles et al. ................. | 227/19 |
| 3,955,581 A | 5/1976 | Spasiano ................. | 128/334 R |
| 4,086,926 A | 5/1978 | Green et al. ............ | 128/334 R |
| 5,032,127 A | 7/1991 | Frazee et al. ............... | 606/143 |
| 5,049,152 A | 9/1991 | Simon et al. ................ | 602/143 |
| 5,104,394 A | 4/1992 | Knoepfler et al. .......... | 606/143 |
| 5,112,343 A | * 5/1992 | Thornton ..................... | 606/143 |
| 5,192,288 A | 3/1993 | Thompson et al . ......... | 606/143 |
| 5,269,792 A | 12/1993 | Kovac et al. ................ | 606/158 |
| 5,330,442 A | 7/1994 | Green et al. ................. | 606/232 |
| 5,336,229 A | 8/1994 | Noda .......................... | 606/144 |
| 5,366,458 A | 11/1994 | Korthoff et al. ............. | 606/151 |
| 5,447,513 A | 9/1995 | Davison et al. .............. | 606/143 |
| 5,527,319 A | 6/1996 | Green et al. ................. | 606/143 |
| 5,578,047 A | * 11/1996 | Taylor ......................... | 606/157 |
| 5,601,573 A | 2/1997 | Fogelberg et al. ........... | 606/143 |
| 5,609,599 A | * 3/1997 | Levin .......................... | 606/153 |

\* cited by examiner

*Primary Examiner*—Gary Jackson
(74) *Attorney, Agent, or Firm*—Robert C. Kain, Jr.; Fleit, Kain

(57) ABSTRACT

The suture clip includes a pair of plates joined together at one end to form a vertex having an acute angle. Each plate, at its remote terminal end, defines an inwardly facing hook. The hook end members establish a clip mouth slightly larger than the diameter of the suture thread such that when the thread is passed through the clip mouth, the thread cannot easily escape entrapment from the central region of the clip. The suture clip may be C-shape, V-shape, broken leg V-shape, heart shape or pentagonal shape. In another embodiment, the clip is a closed loop or elliptical in shape. To enhance operability, the hooks on the C, U or V shaped sutures are disposed on tabs which are laterally displaced with respect to each other such that, upon collapse and closure of the clip plates, the tabs interleave each other and interlock over the opposite clip plate. This feature enhances attachment to suture thread. The method for attachment on suture thread includes providing a clip having several specific features, passing the suture thread through the clip mouth and collapsing the clip plates together over the suture. The enhanced method interleaves terminal edge tabs and interlocks a respective tab over an opposing corresponding clip plate. The surgical appliance for clipping together suture thread includes a suture clip having certain characteristics, a pair of opposing appliance jaws and an elongated mechanical linkage which, upon compression of handle members by a user at a proximal location, the mechanical linkage transfers that force and movement to the compress appliance jaws at a distal end of the appliance thereby closing the suture clip on the suture thread. The enhance threading the suture through the lumen of the clip, an elongated closed loop wire is utilized.

26 Claims, 10 Drawing Sheets

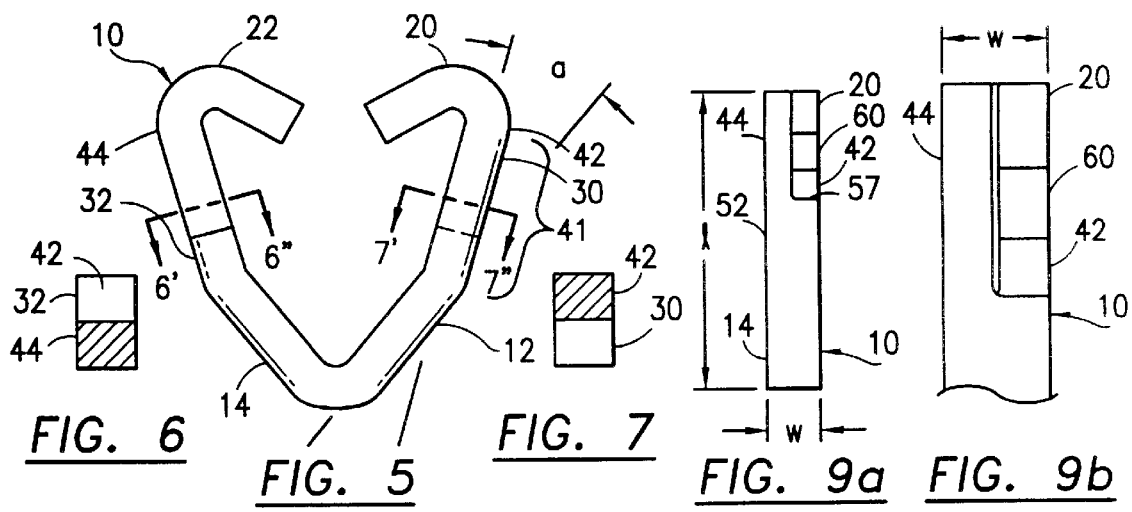
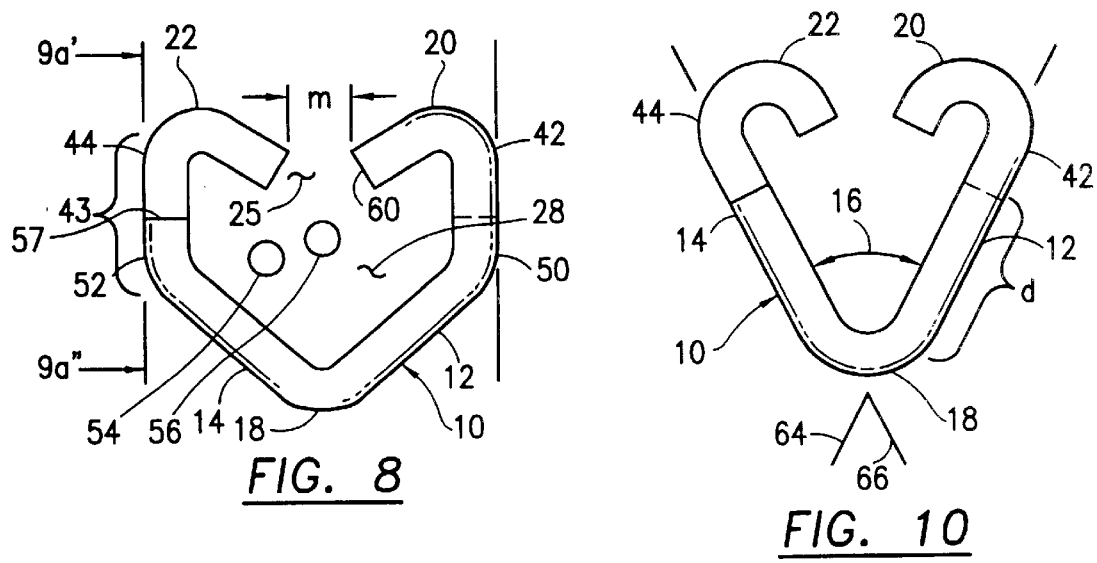
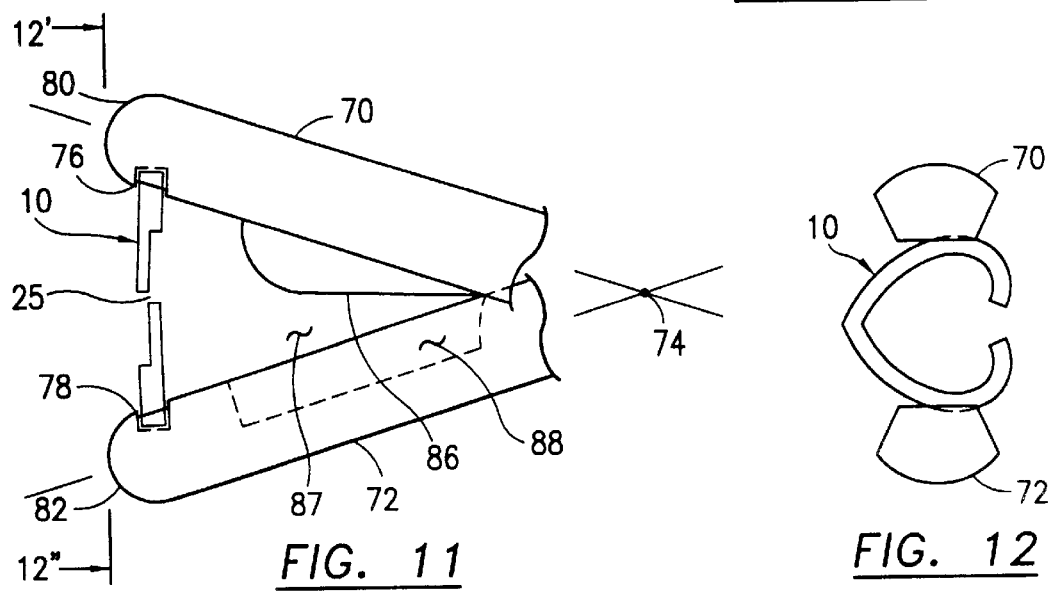

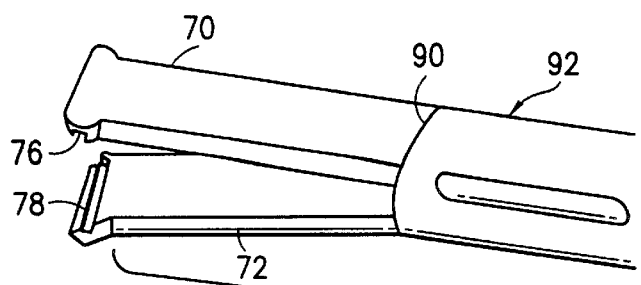
FIG. 14a
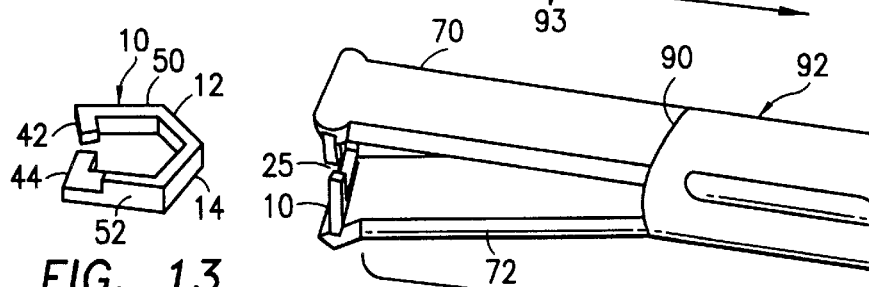
FIG. 13
FIG. 14b
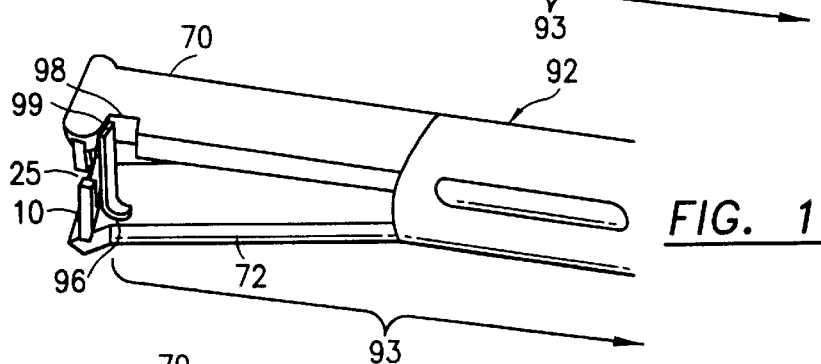
FIG. 15
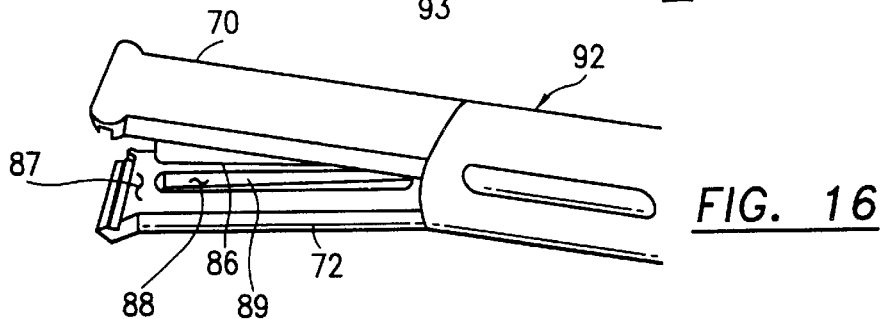
FIG. 16
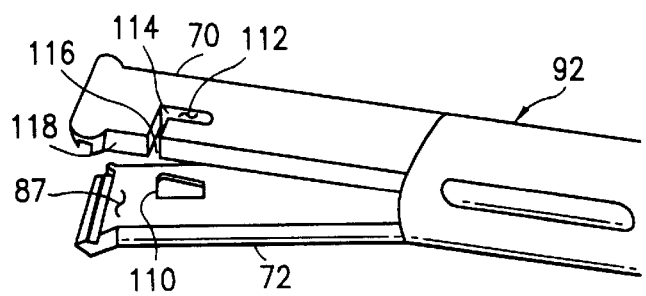
FIG. 17

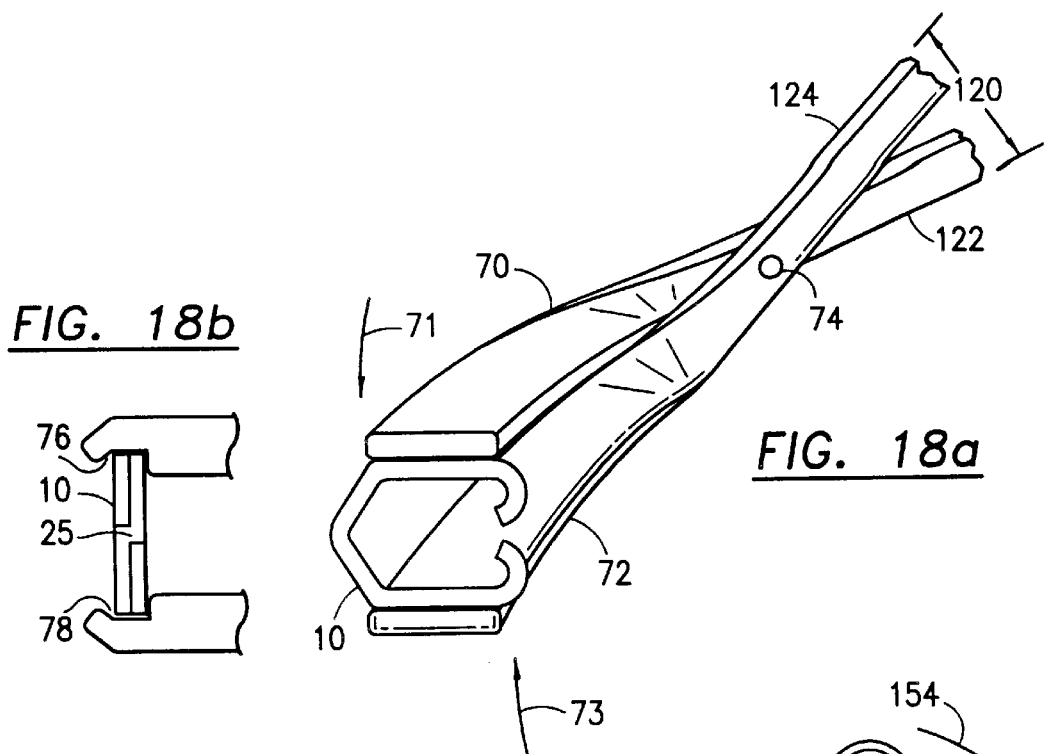
FIG. 18b
FIG. 18a
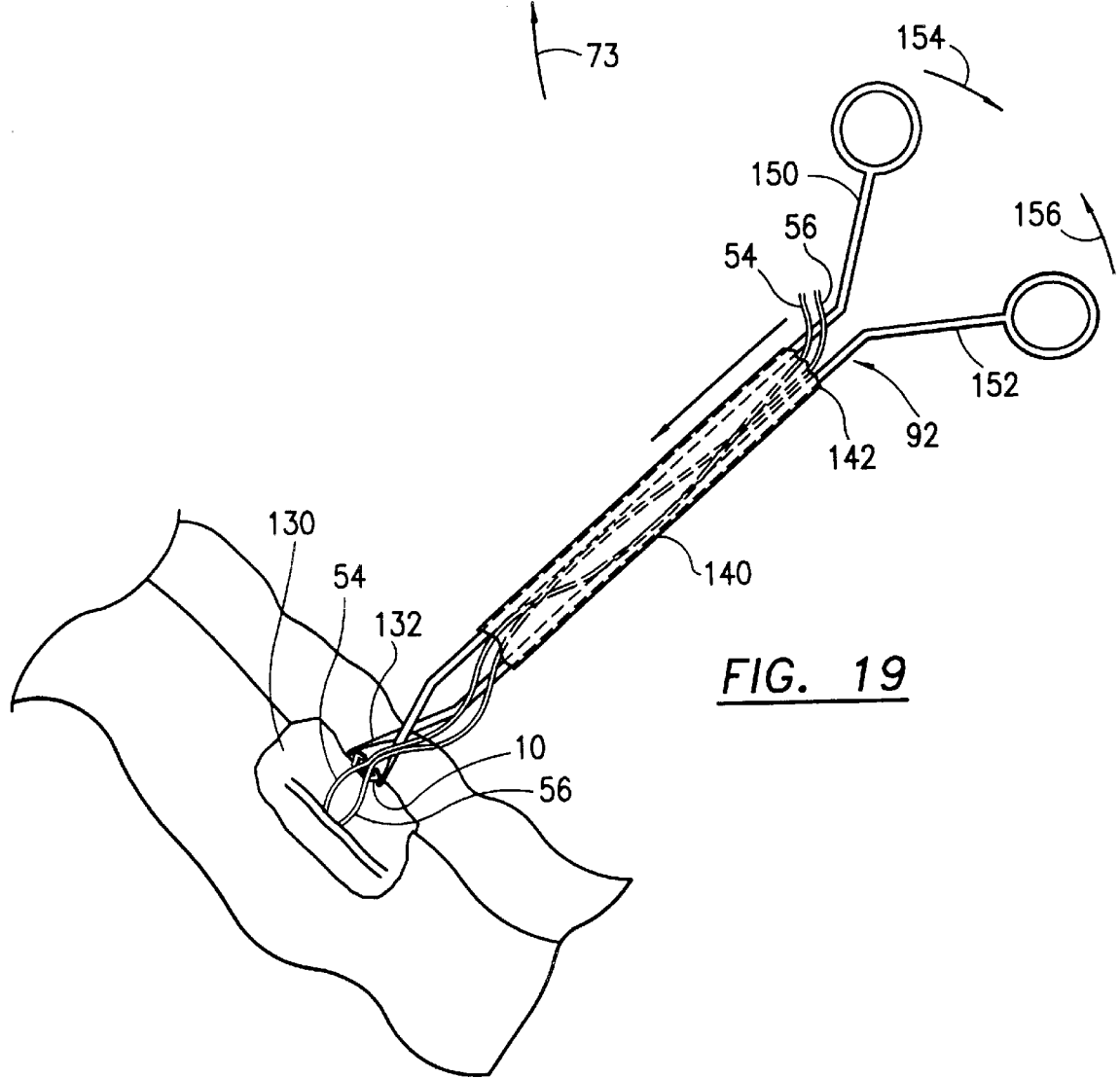
FIG. 19

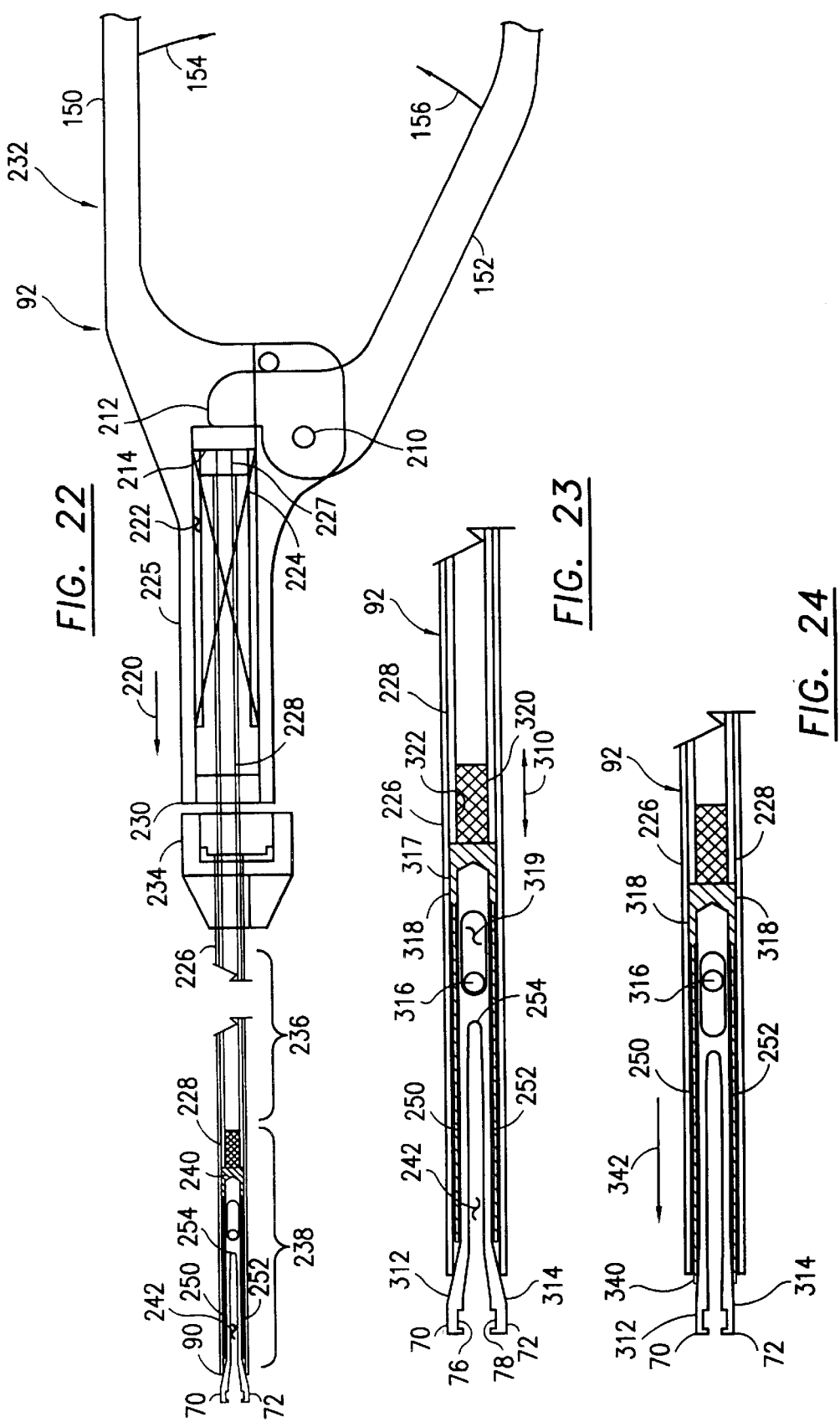

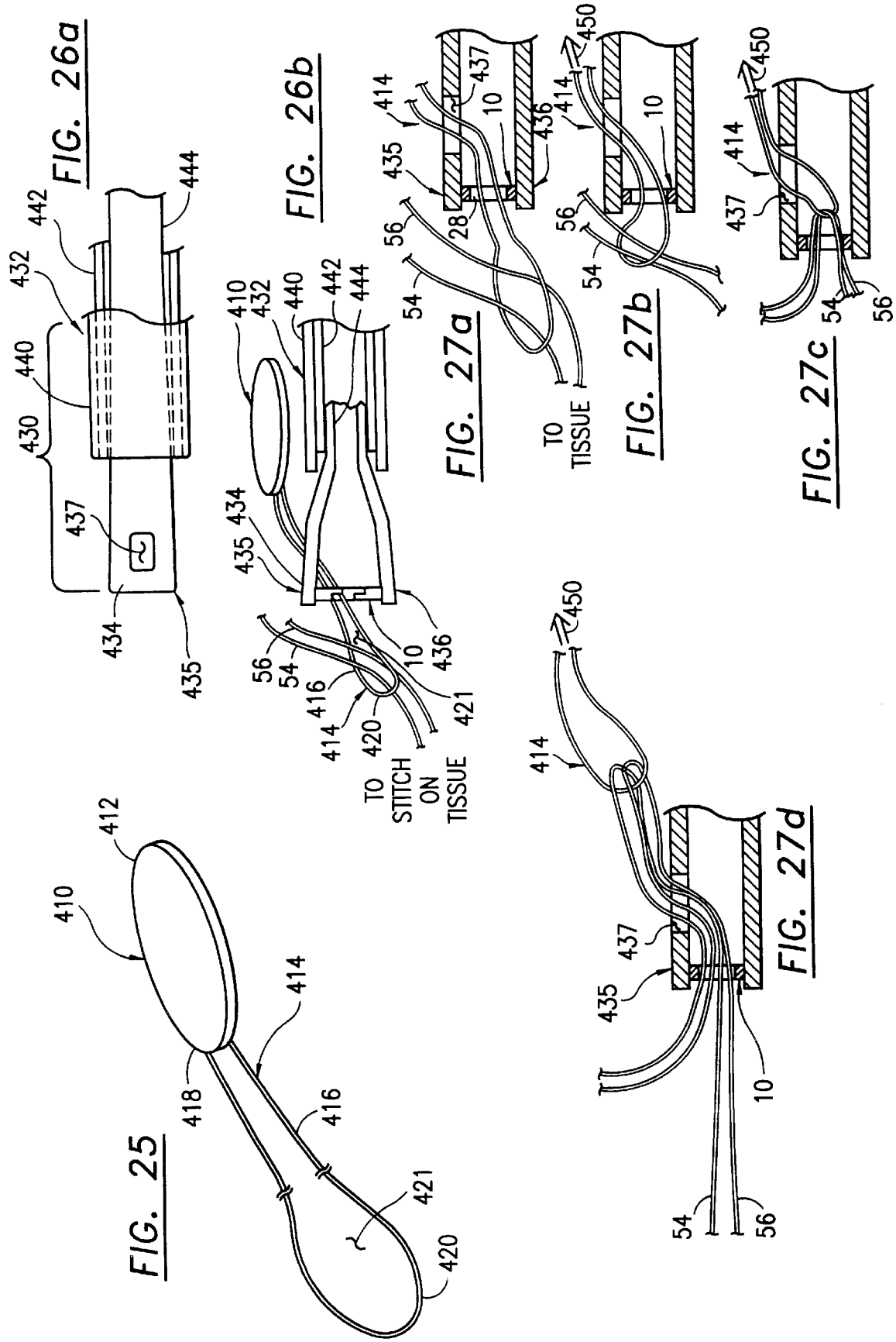

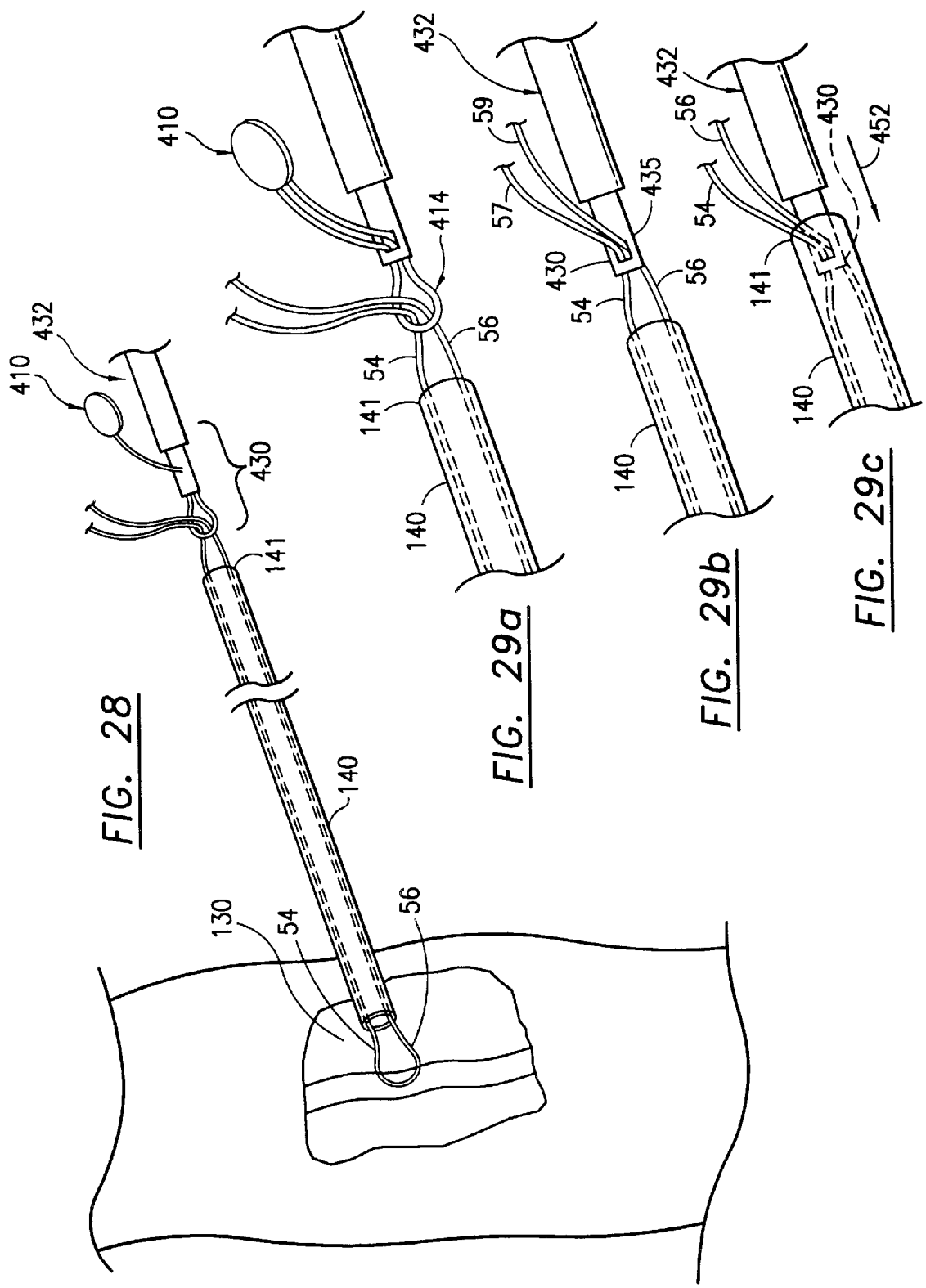

SHAPED SUTURE CLIP, APPLIANCE AND METHOD THEREFOR

The present patent application is a divisional patent application based upon patent application Ser. No. 09/330,439 filed Jun. 11, 1999, now U.S. Pat. No. 6,165,204.

The present invention relates to a generally C-shaped or elliptical shape suture clip, an appliance for utilizing the clip and a method therefor.

BACKGROUND OF THE INVENTION

In minimally invasive surgery, for example, laparoscopic surgery, one of the more difficult, tedious and repetitive procedures involves the tying of knots on suture thread at a distance. Typically, tying of suture knots is done with two legs of the suture thread protruding from a proximal end of a cannula or tube. The inside diameter of a typical cannula ranges from 5 mm to 10 mm. Each throw of the suture knot (usually the knot requires four or five throws) is placed on the thread outside the cannula (outside the body of the patient) and the knot is pushed to its destination through the cannula with a tool commonly called a "knot pusher." Ultimately, the suture knot is tightened on or near the sutured organ, vessel or tissue at the surgical site.

The present invention replaces the need for tying knots on suture thread (and hence the need to utilize knot pushers) during surgical procedures (whether minimally invasive procedures or other types of surgical procedures).

OBJECTS OF THE INVENTION

It is an object of the present invention to provide a suture clip for attachment to suture thread, an appliance for utilizing the suture clip, and a method therefor.

It is another object of the present invention to provide a suture clip which holds the suture as securely as tying a knot on the suture.

It is an additional object of the present invention to provide a generally C-shaped suture clip wherein the C-shape may also be characterized as a V-shape, broken leg V-shape, a heart shape and a pentagonal shape.

It is another object of the present invention to provide an elliptical shaped suture clip.

It is a further object of the present invention to provide a closed loop suture clip and a reading device for the sutures.

It is a further object of the present invention to provide a C or U or V shaped suture clip which defines inwardly facing hooks establishing a clip mouth which hook-defined clip mouth enables entrapment of suture thread in a central region of the clip.

It is an additional object of the present invention to provide a C or U or V shaped suture clip wherein the hooks are laterally displaced and, upon closure of the clip plates, the hooks interleave and interlock over opposite clip plates.

It is another object of the present invention to provide a surgical appliance for utilization of the surgical clip.

SUMMARY OF THE INVENTION

The suture clip includes a pair of plates joined together at one end to form a vertex having an acute angle. Each plate, at its remote terminal end, defines an inwardly facing hook. The hook end members establish a clip mouth slightly larger than the diameter of the suture thread such that when the thread is passed through the clip mouth, the thread cannot easily escape entrapment from the central region of the clip. The suture clip may be C-shape, V-shape, broken leg V-shape, heart shape or pentagonal shape. In another embodiment, the clip is a closed loop or elliptical in shape. To enhance operability, the hooks on the C, U or V shaped sutures are disposed on tabs which are laterally displaced with respect to each other such that, upon collapse and closure of the clip plates, the tabs interleave each other and interlock over the opposite clip plate. This feature enhances attachment to suture thread. The method for attachment on suture thread includes providing a clip having several specific features, passing the suture thread through the clip mouth and collapsing the clip plates together over the suture. The enhanced method interleaves terminal edge tabs and interlocks a respective tab over an opposing corresponding clip plate. The surgical appliance for clipping together suture thread includes a suture clip having certain characteristics, a pair of opposing appliance jaws and an elongated mechanical linkage which, upon compression of handle members by a user at a proximal location, the mechanical linkage transfers that force and movement to the compress appliance jaws at a distal end of the appliance thereby closing the suture clip on the suture thread. The enhance threading the suture through the lumen of the clip, an elongated closed loop wire is utilized.

BRIEF DESCRIPTION OF THE DRAWINGS

Further objects and advantages of the present invention can be found in the detailed description of the preferred embodiments when taken in connection with the accompanying drawings in which:

FIGS. 5, 6 and 7 diagrammatically illustrate a broken leg V-shaped suture clip, a cross-sectional view from the perspective of section line 6'–6", and a cross-sectional view from the perspective of section line 7'–7";

FIGS. 8, 9a and 9b diagrammatically illustrate a pentagonal shaped suture clip (preferred embodiment), a side view of the clip and a detailed side view of the clip showing laterally displaced tab plates;

FIG. 10 diagrammatically illustrates a V-shaped suture clip;

FIGS. 11 and 12 diagrammatical illustrates the jaws of an appliance (side view and end view) utilizing the C-shaped suture clip more specifically illustrated in FIGS. 1, 5, 8 and 10;

FIG. 13 diagrammatically illustrates a perspective view of another C-shaped suture clip;

FIGS. 14a and 14b diagrammatically illustrate a perspective view of a surgical instrument appliance utilizing the surgical clip (FIG. 14a without the clip and FIG. 14b with the clip);

FIGS. 15, 16 and 17 diagrammatically illustrate a perspective view of a surgical instrument appliance with various cutting tools and blades disposed at different locations on the appliance jaws;

FIGS. 18a and 18b diagrammatically illustrate a perspective view and a side view of another appliance utilizing the suture clip;

FIG. 19 is a basic plan view showing basic components and structures of the surgical appliance;

FIGS. 22, 23 and 24 diagrammatically illustrate a surgical appliance for utilizing and attaching the surgical clip to suture threads, a detailed end view showing an "open jaw" position for the surgical appliance and a partially closed jaw configuration;

FIG. 25 diagrammatically illustrates a threading unit (an elongated, closed wire loop);

FIGS. 26a and 26b diagrammatically illustrate a top view and a side view of the appliance jaws without and with the treading unit and suture thread;

FIGS. 27a, 27b, 27c and 27d show various threading stages for the suture thread;

FIG. 28 diagrammatically illustrates threading suture thread onto the clip prior to insertion into a cannula;

FIGS. 29a, 29b and 29c illustrate threading the suture thread and insertion of the threaded clip into the cannula;

DETAILED DESCRIPTION OF THE PREFERRED EMBODIMENTS

The present invention relates to a C-shaped suture clip, surgical appliance and method therefor. Reference herein to a "C-shaped clip" refers to several general C-shapes shown in FIGS. 1, 5, 8, 10 and 13. Specifically, the suture clip may be a C-shape, V-shape, a broken leg V-shape (FIG. 5), a pentagonal shape (FIG. 8) or other type of "heart shape" suture clip that incorporates the specific features discussed hereinafter. Other closed ring shaped clips are shown in connection with FIGS. 31–34. The following Shape Table provides some examples.

| Shape Table |
| --- |
| heart shaped |
| C |
| V |
| broken leg V |
| pentagonal |
| heart |

The suture clip is utilized to attach to suture thread. As discussed earlier in minimally invasive surgery, medical professionals utilize suture threads or sutures to stitch up and close items at the surgical site. See generally FIG. 19. In the present invention, two free ends of a suture thread are attached together via the suture clip. However, it is possible to mount a suture clip on a single piece of thread.

The following Materials Table identifies some exemplary materials for the suture clip.

| Materials Table |
| --- |
| titanium |
| stainless steel |
| tantalum |
| other malleable, bio-compatible metal |

The suture clip is, in a preferred embodiment, a single, integral, one piece structure. The suture clip is generally "heart shaped" or C-shaped in order to retain suture thread in its central, inboard region. FIG. 19 grossly and diagrammatically illustrates the suture clip, the suture thread and the surgical appliance all extending through a cannula from a proximal position near the medical professional to a distal position at the surgical site. Once the thread is placed in the central inboard region of the surgical clip, the suture thread cannot easily escape from that clip region due to inwardly facing hooks on the terminal edge of the suture clip. The size of the clip mouth is important. It is slightly larger than the suture thread diameter. Also, the clip is large enough to be seen (visually identified) by the medical professional without the aid of a scope or magnifying glasses. These concepts are embodied in the clips shown in FIGS. 1, 5, 8, 10 and 13.

Figure 1:
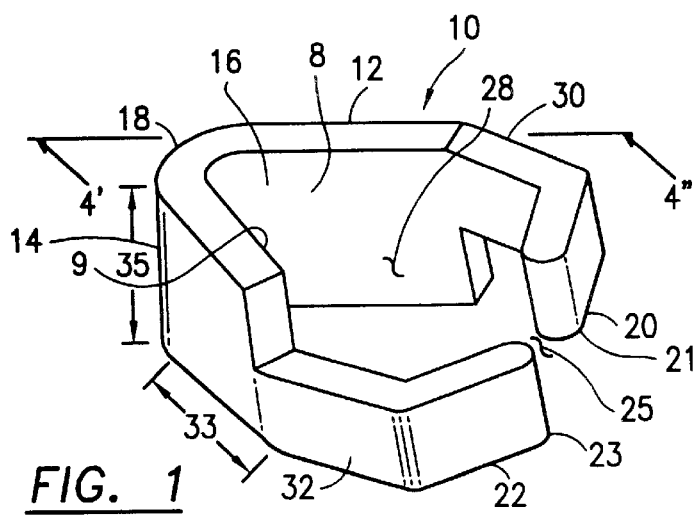
FIGS. 1–3 diagrammatically illustrate a perspective view of the suture clip in a generally fully open, partially closed and fully closed position.
Figure 2:
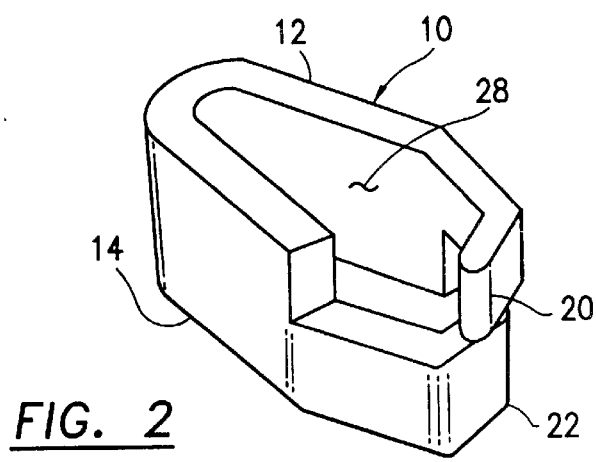
Figure 3:
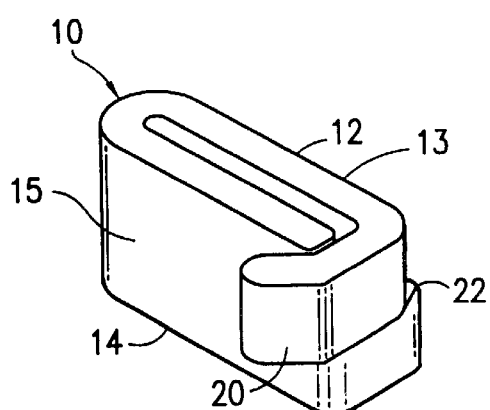

FIGS. 1, 2 and 3 show suture clip 10 in a generally open state, a partially closed state and a fully closed state, respectively. Similar numerals designate similar items throughout the drawings. Suture clip 10 shown in FIGS. 1–3 is a broken leg V-shaped clip and is clearly shown in FIG. 5. FIG. 8 shows a pentagonal shaped clip, FIG. 10 shows a V-shaped clip and FIG. 13 shows a broken leg V-shaped clip or a modified pentagonal clip wherein the side arm plates of the pentagon (which are usually parallel) are angularly disposed inward towards the central region of the clip.

Returning to FIG. 1, clip 10 includes a pair of plates 12, 14 that form a vertex and define a substantially acute angle 16. In a preferred embodiment, clip 10 initially is a solid, planar plate of suitable bio-compatible metal (See Materials Table above) which is rectangularly cut, then bent to form vertex 18 and acute angle 16. Tab segments are cut or punched prior to bending.

An important feature of the present invention is inwardly facing hooks 20, 22 which are disposed along remote terminal edges 21, 23 of clip plates 12, 14, respectively. Hook ends 20, 22 face each other and form a clip mouth 25 which is slightly larger than the suture thread. In this configuration, when suture thread is feed through clip mouth 25 and placed in central region 28, it is difficult, if not impossible, for the suture thread to escape from central clip region 28.

The discussion herein of the shape of the clip (C, V, or otherwise) ignores the shape of hook end shape 20, 22.

Clip 10 in the embodiment illustrated in FIG. 1, is a broken leg V-shaped clip similar to that shown in FIG. 5. However, in FIG. 5, the extender tabs carrying hook ends 20, 22 do not extend the longitudinal extent of the broken leg segment. This feature will be discussed later in connection with FIG. 5. In FIG. 1, clip 10 is characterized as a "broken leg V-Shape" because clip plates 12, 14 initially form a V-shaped figure leading to broken leg segments 30, 32. Clip plates 12, 14 have a longitudinal extent 33 and a lateral extent 35. Broken leg segments 30, 32 protrude as tabs from major plate segments 12, 14. The tabs terminate in hook ends 20, 22. The tabs or broken leg segments 30, 32 are laterally displaced with respect to each other (over lateral dimension 35) such that inwardly facing hook ends 20,22, upon closure, interleave each other.

FIG. 2 diagrammatically illustrates hook ends 20, 22 interleaved with respect to each other during partial closure of plates 12, 14. This closure essentially captures one or more suture threads in interior clip region 28. In FIG. 3, the plates 12, 14 of clip 10 are completely collapsed together such that the inboard surface of clip plate 12 is generally adjacent the inboard surface of clip plate 14, and hook end 20 is wrapped around and interlocked over outboard surface 15 of clip plate 14. In a similar manner, hook end 22 is wrapped around and interlocked on exterior surface 13 of clip plate 12.

Figure 4A:
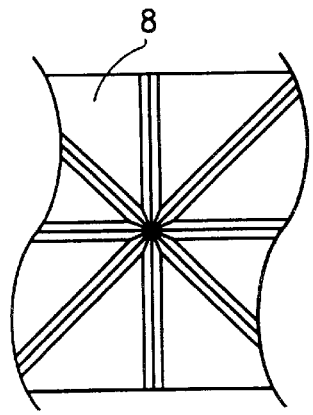
FIGS. 4a, 4b and 4c diagrammatically illustrate the inboard grip surface (preferred, but not required, embodiment) for the suture clip.
Figure 4B:
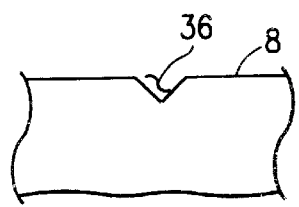
Figure 4C:
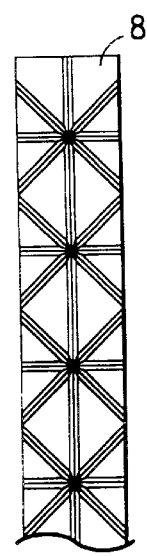

To enhance the grip of suture clip 10 on the suture thread, inboard surfaces 8, 9 of clip plates 12, 14 carry a groove pattern thereon. FIGS. 4a, 4b and 4c diagrammatically illustrate one type of groove pattern on inboard face or surface 8. FIG. 4a shows a plan view of the groove pattern in a general "asterisk" shaped form. FIG. 4b shows that each groove in the pattern has a triangular cross-section (beneath the inboard clip surface) as shown by V-shaped cutout 36. FIG. 4c diagrammatically shows a plurality of "asterisk" grip patterns on interior surface 8 of the clip plate. Groove surfaces for the suture clips are better illustrated and discussed in detail in a patent application entitled "Surgical Instrument for Stapling and Cutting Blood Vessels and Organic Structures Method Therefor and Surgical Clips" filed on Jan. 22, 1999 and assigned Ser. No. 09/235,412. Patent application Ser. No. 09/235,412 is incorporated herein by reference thereto. Other grip patterns may be utilized. These other group patterns are discussed in a summary manner and patent application Ser. No. 09/235,412.

As discussed briefly above, the suture clip of the present invention may be generally characterized as C-shaped, however, V-shaped, broken leg V-shaped, heart shaped and pentagonal shaped suture clips embodying the important characteristics of the present invention are illustrated herein. Currently, the preferred embodiment is a pentagonal shaped suture clip best shown in FIG. 8.

FIG. 5 diagrammatically illustrates clip 10 having clip plates 12 and 14. The clip plates 12, 14 formed the base of the V-shape. Extending longitudinally from base plate portions 12, 14 are broken leg plate portions 30, 32. Broken leg portions 30, 32 extend longitudinally a distance 41 from the vertex. As shown in FIG. 5, part of broken leg plate segments 30, 32 have been altered or cut to form remote terminal tabs 42, 44.

FIG. 6 diagrammatically illustrates a cross-sectional view from the perspective of section line 6'–6" in FIG. 5 and shows that tab plate segment 44 extends longitudinally from end surface portion 46 of broken segment 32. In a similar manner, FIG. 7 is viewed from the perspective line of section line 7'–7" in FIG. 5 and shows a tab plate or segment 42 extending longitudinally beyond broken segment 30. In order to illustrate the lateral displacement of tab plates 42, 44, tab plates which are further away from the viewer are shaded. Accordingly, tab plate 44 carrying hook end 22 is shaded but tab plate 42 carrying hook end 20 is not shaded.

Broken leg plate segment 30 is angularly offset by angle "a" from clip plate 12. In other words, broken segment 30 and hence tab plate 42 is offset by an inboard angle a offset with respect to clip plate 12.

FIG. 8 diagrammatically illustrates the pentagonal shaped clip 10. Pentagonal clip 10 includes plates 12, 14 which form the base of the initial V-shape of the clip, parallel plate segments 50, 52 extend therefrom, tab plates 42, 44 extend from segments 50, 52 and remotely disposed, inwardly facing hook ends 20, 22 extend from the tabs 42, 44. Hook ends 20, 22 face inboard towards inboard clip region 28. In FIG. 8, suture threads 54, 56 are caught or entrapped within central clip region 28. Mouth 25, in a preferred embodiment, is slightly larger than the diameter of suture thread 54, 56. The mouth 25 has a width or a dimension m which is designed to be slightly larger than the diameter of suture thread 54, 56. This enables clip 10 to capture and retain suture thread 54, 56 in its central region while the clip retaining appliance is fed through the cannula and to the surgical site. The clip and threaded thread is fed through the cannula. See generally FIG. 19. FIG. 8 shows that tab plates 42, 44 are configured to begin approximately mid-way through the longitudinal extent 43 of the parallel plate leg segment 52. In other words, parallel plate segment 52 has a step down or edge 57 which defines the forward portion of the tab plate 44 nearest vertex 18 of clip 10. The aft end of the tab defines the inwardly facing hook.

FIG. 9a is a view of clip 10 from the perspective of section line 9a'–9a" in FIG. 8. Tab section 44 and step 57 is shown for plate segment 52. End hook 20 is shown as having terminal end 60. Tab plate 42 is also shown as being laterally displaced with respect to tab plate 44.

FIG. 9b shows a detail of the lateral displacement of the tabs over clip thickness or distant w. Tab plate 42 is laterally disposed apart from tab plate 44 such that one tab, upon collapse of clip plate 12, 14, passes the other tab and the tabs interleave with respect to each other and interlock on the opposite plate in a preferable manner as shown in FIG. 2 and 3. The spacial distance illustrated in FIG. 9b between tab plates 42, 44 may be exaggerated.

FIG. 10 shows a V-shaped suture clip 10. The V-shape is apparent because clip plates 12, 14 establish acute angle 16 and generally extend in the same angularly disposed plane from vertex 18 to the aft end of the clip. In other words, clip plane 64 is angularly disposed with respect to clip plane 66 and those planes encompass clip plates 12, 14, respectively. At a certain longitudinal distance d, plates 12, 14 are laterally cut away or otherwise trimmed to form tab plates 42, 44. Tab plates 42, 44 are further formed to provide inwardly facing hook ends 20,22. These features may be cut away from a singular plate of bio-compatible material and the hooks may be formed on a mandril.

The following Clip Dimension Table shows exemplary dimensions for the suture clip.

| Clip Dimension Table | | |
| --- | --- | --- |
| clip shape | mouth dia. (m) | closed length (l) |
| broken leg V | 0–20 size suture (e.g., 0.05 in.) | 0.114 in. |
| pentagonal | 0–20 size suture | 0.138 in. |
| V | 0–20 size suture | 0.114 in. |

The following Dimension Table for the broken leg V clip provides some examples of relative dimensions and size for the broken leg V clip.

| Dimension Table-Broken Leg V Clip | |
| --- | --- |
| leg offset angle a | about 18 degrees |
| width | about 0.04 in. |
| half width at aft end of tab | about 0.02 in. |

Since the suture clip shown in FIGS. 1, 5, 8, 10 and 13 has collapsible plate segments, these plates provide jaw members which close on the suture thread extending through central region 28. See particularly FIG. 8. The jaw members of suture clip 10 are different than appliance jaws discussed below in connection with FIGS. 11–24.

FIGS. 11 and 12 diagrammatically illustrate the distal end of a surgical appliance which is utilized to place clip 10 on suture thread. In FIG. 11, the appliance includes closeable appliance jaws 70, 72. Jaws 70, 72 rotate about pivot point 74. Clip 10 is disposed in a clip channel 76, 78 near distal terminal ends 80,82 of appliance jaws 70, 72. In practice, suture thread is fed into clip mouth 25 prior to insertion of the surgical appliance carrying appliance jaws 70, 72 through a cannula into the surgical site. After clip 10 reaches the appropriate location on the suture thread, appliance jaws 70, 72 are closed and the surgical thread is caught by collapsing plate members of clip 10. Thereafter, the medical professional moves appliance jaws 70, 72 an appropriate distance and places the suture thread near blade 86. Blade 86 extends inwardly into the throat 87 of appliance jaws 70, 72. Blade 87 also moves, upon jaw closure, into cutout anvil region 88. Anvil region 88 is formed in the throat region of appliance jaw 72. The suture thread is caught between blade 86 and anvil region 88 and is thereby cut by the blade carrying jaw.

FIG. 12 diagrammatically shows upper and lower appliance jaws 70, 72 with the heart shaped suture clip 10 therein. The clip shown in FIG. 12 has clip plates that are formed as a continuous curve. Hence, clip 10 in FIG. 12 may be considered a "heart shape" rather than a V-shape, pentagonal shape or as otherwise illustrated in this specification.

FIG. 13 shows suture clip 10 having collapsible clip plates 12, 14, clip leg segments 50, 52 and half height tab plates 42, 44. Plate leg segments 50, 52 are angularly disposed inward with respect to each other. Accordingly, clip 10 shown in FIG. 13 is a modification of the pentagonal clip 10 shown in FIG. 8.

FIGS. 14a and 14b show upper and lower appliance jaws 70, 72 and distal end 90 of surgical appliance 92. Clip 10 is placed in clip carrying channels 76, 78. Appliance 92 is an elongated appliance that has a longitudinal aspect 93. As shown in FIG. 14b, clip 10 is placed laterally or generally perpendicular to the longitudinal aspect 93 of surgical appliance 92. The medical professional places clip 10 in channels 76, 78, feeds the suture thread into clip mouth 25 and inserts the threaded clip end of appliance 92 into the cannula generally shown in FIG. 19.

FIG. 15 shows lower appliance jaws 72 carrying a blade member 96 which is normal to longitudinal aspect 93 of surgical appliance 92. Blade member 96 is disposed in a cut-out 98 on upper appliance jaw 70. In use, the medical professional places the surgical thread in cut-out 98 about the top end 99 of blade 96 and then runs the suture thread through mouth 25 of clip 10. Alternatively, the medical professional places the suture in mouth 25 of clip 10 and then runs the suture around top end 99 of blade member 96.

FIG. 16 diagrammatically shows blade 86 extending longitudinally and protruding normally into throat 87 formed by appliance jaws 70,72. Blade 86, when jaws 70, 72 close, moves into anvil channel 88. Anvil channel 88 may include an anvil surface 89 (or the opposing planar surface forming anvil channel 88). In other words, blade 86 may need an anvil surface 89 against which to pinch and thereafter cut the suture thread.

FIG. 17 shows an upstanding blade member 110 protruding above appliance jaw 72 and throat 87. Blade 10 extends into cutout region 112 formed in upper appliance jaw 70. Surface 114 defining cutout 112 may provide an anvil surface for blade 110. Cutout 112 further includes a cutout mouth 116. Cutout mouth 116 provides an opening from lateral edge 118 of upper appliance jaws 70. This permits the medical professional to run the suture thread through cutout mouth 116 and into cutout region 112. Upon closure of upper and lower appliance jaws 70, 72, blade 110 slices the suture thread either independently or in conjunction with anvil surface 114.

FIGS. 18a and 18b diagrammatically show another configuration of the distal end of the surgical appliance. Particularly, upper and lower appliance jaws 70, 72 capture pentagonal clip 10 and clip channels 76, 78. Appliance jaws 70, 72 pivot about pivot point 74 based upon compressive force closing the distance 120 between jaw extensions 122 and 124. Jaw extensions 122, 124 extend in an aft direction away from the distal end and towards the medical professional beyond pivot point 74 and are generally integral with appliance jaws 70, 72.

FIG. 19 grossly illustrates surgical appliance 92 and the application of clip 10 on suture thread 54, 56. Suture thread 54, 56 (which is a single thread), has been placed at surgical site 130 by the medical professional. Clip 10 has been mounted at the distal end 132 of appliance 92. Suture threads 54, 56 have been fed through clip mouth 25 (FIG. 18b) and the threaded clip carrying distal end 132 of surgical appliance 92 has been fed through cannula 140. Suture 54, 56 may or may not extend from proximal end 142 of cannula 140.

Upon placement of clip 10 on the suture thread at distal end 132 near surgical site 130, the medical professional applies a compressive force to handle members 150, 152 as shown by arrows 154, 156. A mechanical linkage (described later or as known by persons of ordinary skill in this technology) transfers the compressive force and movement 154, 156 to the distal end of the appliance thereby closing appliance jaws 70, 72 as shown by arrows 71, 73 in FIG. 18a. FIG. 19 is a gross illustration of surgical appliance 92.

Figure 20:
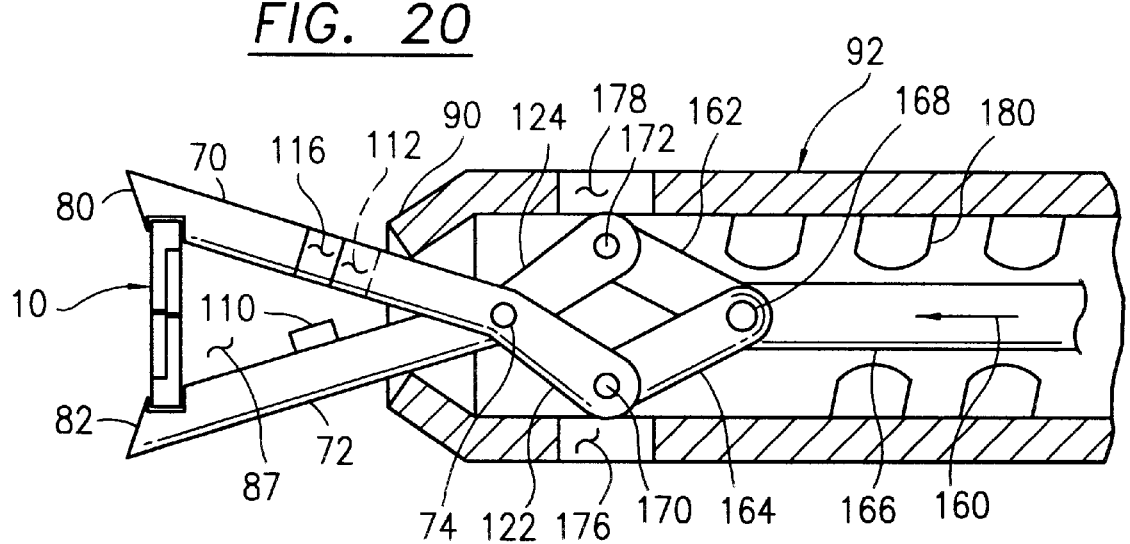
FIGS. 20 and 21 diagrammatically illustrate another surgical appliance utilizing the suture clip.

FIG. 20 diagrammatically illustrates one type of mechanical linkage to transfer compressive force 54, 56 into appliance jaw compressive force to close appliance jaws 70, 72 on clip 10. In this embodiment, the compressive force is converted into longitudinally directed motion and force 160. Appliance jaws 70, 72 pivot about point 74. The jaws have aft extending members 122, 124. Mechanical linkage members 162, 164 are connected at their proximal end to longitudinally moveable bar or rod 166. Mechanical links 162, 164 are rotatably mounted at point 168 to longitudinally moveable bar 166. When bar or rod 166 moves forward toward distal end 90 of surgical appliance 92, as shown by arrow 160, mechanical linkage bars 162, 164 transfer that longitudinal movement into lateral movement of appliance jaw extenders 122, 124. This lateral movement is achieved due to the mechanical and rotative connection at linkage points 170 and 172 of jaw extenders 122, 124. Surgical appliance 92 has cutouts 176, 178 which permit jaw extenders 122, 124 to extend laterally with respect to the longitudinal aspect of surgical appliance 92. When jaw extenders 122, 124 move laterally due to the mechanical linkage conversion of longitudinal movement into lateral movement, the distal ends 80, 82 of appliance jaws 70, 72 close, thereby collapsing suture clip 10 upon the suture. Of course, reverse longitudinal movement in a direction opposite arrow 160 causes mechanical links 162, 164 to pull jaw extends 122, 124 laterally inboard toward the axial centerline of surgical appliance 92. This mechanical conversion of outboard longitudinal force and direction into inboard lateral force causes appliance jaws 70, 72 to open with respect to each other. Surgical appliance 92 may be threadably attached by female threads 180 to other distally disposed components of surgical appliance 92.

Figure 21:
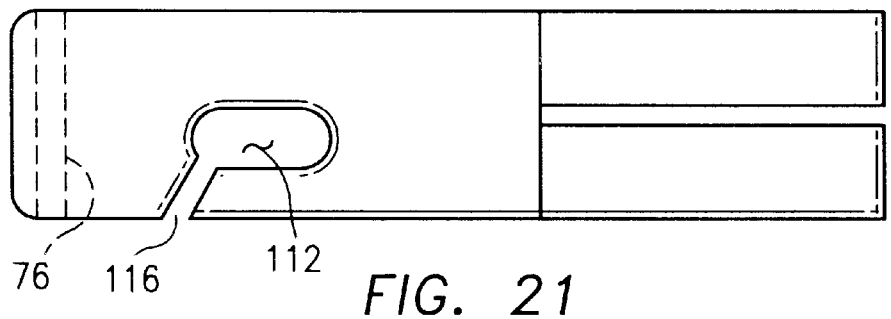

FIG. 21 diagrammatically illustrates upper jaw member 70 having cutout 112 and cutout mouth 116. Suture thread is captured and fed through cutout mouth 116 into cutout 112. Blade 110 (FIG. 20) moves into cutout 112 and cuts the suture.

FIGS. 22, 23 and 24 diagrammatically illustrate the principal elements of surgical appliance 92 (a currently preferred embodiment), a detailed view of the distal end of the surgical appliance when the appliance jaws are fully open and a detailed view of the distal end of the surgical appliance when the appliance jaws are partially closed. These figures illustrate another type of mechanical linkage to transfer handle movement into appliance jaw movement.

FIG. 22 shows handle members 150, 152 pivotally mounted about pivot point 210 to each other. Upon compression and movement in the direction shown by arrows 154, 156, actuator tab 212 of handle member 152 moves forward toward distal end 90 of surgical appliance 92. Forward movement of actuator member 212 moves piston head 214 in a forward direction, shown by arrow 220. Piston head 214 is mounted in a chamber 222 and is mechanically coupled to actuator rod 227. Piston head 214 is biased in a rearward direction by spring member 224 which is diagrammatically illustrated in FIG. 22.

Piston 214 moves actuator pin 227 longitudinally forward towards the appliance's distal end with respect to outer static housing 225. The pin is mounted in a static tube. This forward movement of actuator rod or pin 227 with respect to static housing 225 is applied to moveable rod 228 and is carried to distal end 230 of handle section 232, through coupler 234, over an extended length portion of surgical appliance 92, diagrammatically illustrated as longitudinal length 236, to the distal end region 238. At distal end 238, longitudinally moveable rod 228 terminates and an appliance jaw casement member 240 defines an outboard, elongated cavity 242 within which appliance jaws 70, 72 are mounted. The distal end of the jaws are spring loaded. In this embodiment, appliance jaws 70, 72 have inwardly extending base elements 250, 252 which are joined together at joint 254. Casement 240 moves longitudinally with respect to static, elongated housing 226.

FIG. 23 shows a detail view of distal end 238 of surgical appliance 92. Essentially, longitudinally moveable tube element 226 moves forward and aft in the direction shown by double headed arrow 310 based upon the compression or release of handle members 150, 152. Of course, longitudinal movement of casement 318 occurs with respect to the fixed position of static support tube 226. Appliance jaws 70, 72 have outer or lateral cam surfaces 312, 314 which ride within the distal end portions of casement 318. The cam surfaces define the speed and distance of closure of clip channels 76, 78. The slope of the cam surface defines the speed of closure. The lateral size or dimension of the jaw and cam define one-half of the closure distance. Hence, the speed and distance of closure of channels 76, 78 is directly related to the speed and distance of closure of a clip.

Appliance jaws 70, 72 are defined at the distal end of extend elements 250, 252. Elements 250, 252 are joined together at point 254. To secure jaw appliance elements 250, 254, a pin, bolt or other lateral mount 316 extends through the base of appliance jaw elements 250, 254 through channel 319 and into the static, non-moveable tubular housing 226. Jaw casement 318 may include a male threaded element 320 at its proximal end which threadably attaches to a female threaded element 322 at the distal end of moveable rod 228. Movable rod 228 rides within static support tube 226 and further rides motivates appliance jaw casement 318. Appliance jaw casement 318 has a strong distal end segment 340 which resists lateral, outboard force of the clip carrying jaws.

Upon forward movement of actuator tab 212 of handle member 152, piston 124 impacts lead pin 227. Lead pin 227 forces movable rod 228 to move forward in direction shown by arrow 220. See FIG. 22. Rod 228 is enclosed by a stationary or static tube 226.

FIG. 23 shows rod 228 terminating and a screw thread plug 320. Threaded plug 320 is mounted to proximal end 317 of movable casement 318. Jaw appliance extender elements 250, 252 are fixed with respect to outer static tube 226 via lateral pin or mount 316. However, jaw casement 318 moves forward due to the forward movement of movable rod 228. This forces the distal end element 340 of casement 318 to move forward in direction 342 shown in FIG. 24. As a result, the forward movement of distal end 340 of casement 318 causes closure of appliance jaws 70, 72. Jaws 70, 72 are fixed with outer static tube 226. Essentially, casement end 340 acts on cam surfaces 312, 314 of appliance jaws 70, 72.

Other types of mechanical linkage elements may be utilized to affect closure of appliance jaws 70, 72.

Further, surgical appliance 92 may be equipped with automated surgical clip loaders. The following patents show automated surgical clip loaders and the content of these patents is incorporated herein by reference thereto.

Automated Surgical Clip Loaders 3,665,924 to Noiles 3,675,688 to Bryan 3,735,762 to Bryan 3,740,994 to DeCarlo 3,819,100 to Noiles 3,955,581 to Spasiano et al.

4,086,926 to Green et al.

5,032,127 to Frazee et al.

5,049,152 to Simon et al.

5,104,394 to Knoepfler 5,192,288 to Thompson et al.

U.S. Pat. No. 5,269,792 to Kovac et al.

U.S. Pat. No. 5,336,229 to Noda

U.S. Pat. No. 5,447,513 to Davison et al.

U.S. Pat. No. 5,527,319 to Green et al.

U.S. Pat. No. 5,601,573 to Fogelberg et al.

A further example of a surgical appliance wherein a moveable tube operates on the outer surface of appliance jaw is shown in U.S. Pat. No. 3,777,538 to Weatherly et al.

FIG. 25 diagrammatically illustrates a threaded unit 410 which includes, in the illustrated embodiment, a flat disc 412, generally the size of an adult's thumb print, and an elongated closed loop 414 of wire 416. Wire 416 is spring wire. The forward end region preferably is a relatively large circle for the tear drop shaped loop. The large end circle is large compared to the size of lumen 28 in clip 10 (FIG. 2). Both structures have substantially the same diameter. Currently, the elongated closed loop 414 is about 1–2 inches in length from forward end 418 of finger disc 412 to forward loop end 420 of closed loop wire 416.

FIG. 26a diagrammatically illustrates distal end 430 of appliance 432 and particularly the top side 434 of appliance jaws 435.

As best shown in the side view of FIG. 26b appliance jaws 435, 436 are upper and lower appliance jaws. Outboard surface 434 in FIG. 26a includes a cutout or pass through 437. As discussed earlier herein, appliance jaws 435, 436 are closed based upon forward movement of longitudinally movable jaw actuator 440. Longitudinally movable jaw actuator 440 rides over stationary elongated tube 442. The rearward extending member 444 of jaw 435 is diagrammatically illustrated to the right in FIG. 26a.

FIG. 26b diagrammatically shows threaded unit 410 in the initial stages of threading suture thread 54, 56 through clip 10. Clip 10 is retained in lateral channels along the inboard surfaces of appliance jaws 436, 438. Greater detail for these inboard clip retaining channels is shown in connection with FIG. 11.

Elongated closed loop wire 414 is fed or passed through cutout 437 in outer surface 434 of upper appliance jaw 435. Thereafter, elongated closed loop wire 414 is fed or passed through the lumen of clip 10. As best shown in FIG. 8, clip 10 has a lumen or central region 28. Thereafter, forward end 420 of closed wire loop 414 extends outboard from the distal ends of appliance jaws 435, 436.

While the surgical appliance is outboard of the cannula during minimally invasive or endoscopic surgery, the surgeon or other medical professional feeds the proximal ends of sutures 54, 56 through opening 421 of closed wire loop 414. As discussed earlier in connection with FIG. 19, suture 54, 56 is really a single thread having a portion thereof passed through a tissue at a surgical site. Accordingly, although the single thread suture is utilized, two end segments 54, 56 are acted on by the medical professional.

FIG. 27a diagrammatically illustrates a portion of appliance jaws 435 and 436. In this illustrated embodiment, closed wire loop 414 passes through cutout 437 and clip lumen 28 of clip 10.

In FIG. 27b, closed wire loop 414 is pulled rearward as shown by arrow 450 thereby drawing suture thread 54, 56 inboard towards the lumen of clip 10.

In FIG. 27c, closed wire loop 414 is pulling suture thread 54, 56 through the lumen of clip 10 and is about to pull suture thread 54, 56 through cutout 437.

FIG. 27d shows closed loop elongated wire 414 having pulled suture thread 54, 56 through the lumen of clip 10 as well as through cutout 437 in the upper appliance jaw 435.

FIG. 28 diagrammatically illustrates the treading operation in accordance with the principles of the present invention. A surgical site 130 is diagrammatically illustrated and suture thread 54, 56 has been threaded or passed through a vessel or other organic structure at surgical site 130. Suture thread 54,56 passes through elongated cannula 140. The distal end 430 of surgical appliance 432 and threading unit 410 is diagrammatically illustrated at or near proximal end 141 of cannula 140.

FIG. 29a diagrammatically illustrates cannula 140, proximal end 141of that unit, and suture threads 54, 56 passed through elongated closed loop wire 414 of threading unit 410. In general, the illustration in FIG. 29a is similar to that shown in FIGS. 26b, 27a and 27b.

FIG. 29b shows suture thread 54, 56 passed through the opening in appliance jaw 435 at distal end 430 of surgical appliance 432. Terminal ends 57, 59 of suture 54, 56 are free ends and are available to be grasped by the medical professional.

In FIG. 29c, distal end 430 of surgical appliance 432 has been inserted into proximal end 141 of cannula 140. Suture thread 54, 56 is retained in a generally stationary position as distal end 430 of clip surgical appliance 432 is inserted through cannula 140 to surgical site 130. This longitudinal movement is generally shown by insertion arrow 452.

Figure 30A:
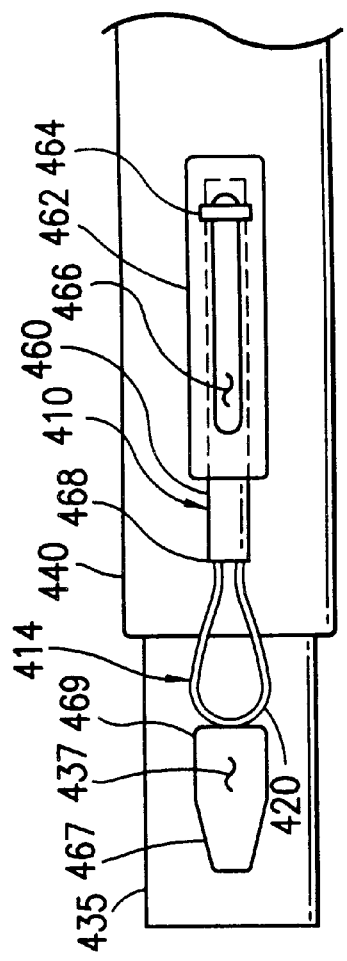
FIGS. 30a, 30b and 30c diagrammatically illustrate a movably mounted threading unit.

FIGS. 30a, b and c diagrammatically illustrate a movably attached threading unit 410. Threading unit 410 has an elongated, movable base member 460 that moves within a channel defined by stationary cover member 462. An operator actuator button, bar, tab or stub 464 is attached to base member 460 and protrudes above longitudinal opening 466 in cover 462. The closed loop elongated wire 414 is attached to the forward end 468 of base member 460.

Other channel and movable member structures may be utilized. For example, two facing and opposing, elongated C-shaped or U-shaped channel members may capture side edges of the elongated, rectangular movable member. In this manner tab 464 and cutout 466 are eliminated. The user simply pushes the member 460 forward.

Upper appliance jaw 435 includes a cutout 437 that has a laterally narrow forward end 467 and a laterally wider rearward end 469. The laterally wider rearward end 469 of cutout 437 permits the laterally wider front end portion of closed wire loop 414 to initially pass into cut out 437. The laterally narrow forward end 467 of cutout 437 captures the wider forward end 420 and threads forward end 420 of closed wire loop 414 beneath upper appliance jaw 435.

Figure 30B:
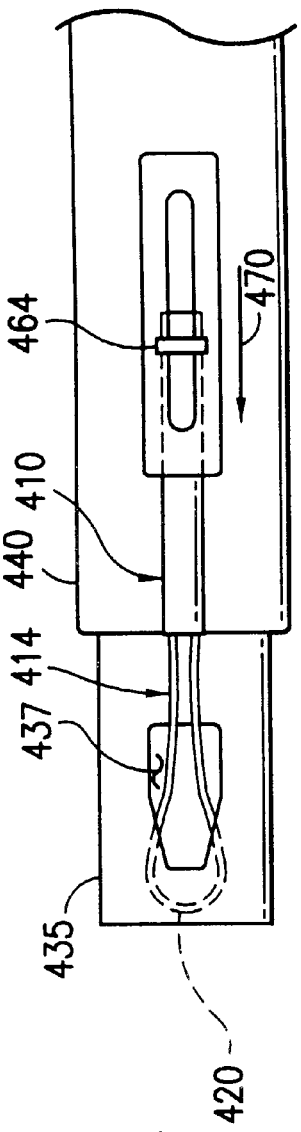

In FIG. 30b, the operator has moved operator actuator member or tab 464 in the direction shown by arrow 470 thereby moving and threading forward end 420 of elongated closed loop wire 414 into cutout 437.

Figure 30C:
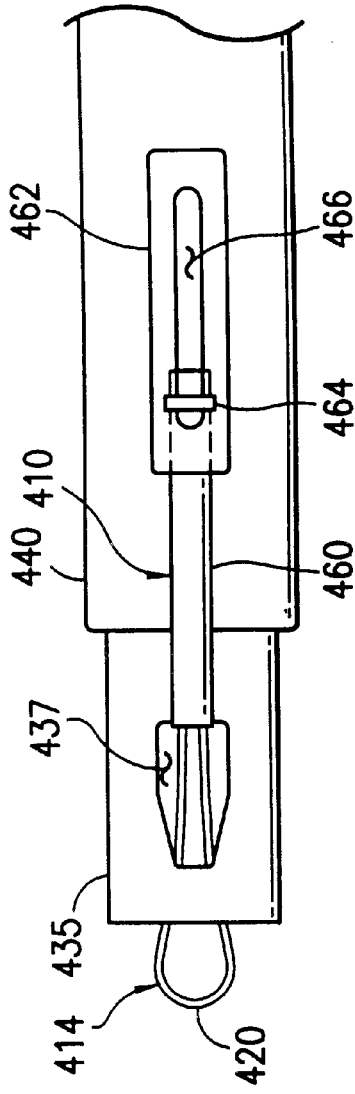

In FIG. 30c, operator tab 464 is at its forward end position of cutout 466 and stationary cover 462. At this position, base member 460 is fully extended. Forward end 420 of elongated closed loop wire 414 is fully extended and passes through appliance jaw cutout 434 and also passes through the lumen of the clip. In a general sense, FIG. 37c shows the forward position of a movably attached threading unit 410 and FIG. 26b shows a forward position of a free standing threading unit 410. However in FIG. 26b, threading unit 410 is an independent, discrete unit or element as compared with member 460 movably mounted on the surgical appliance.

FIGS. 31 through 34 diagrammatically illustrate various forms of closed loop suture clips. With the advent and implementation of threading unit 410, it is now possible to provide a suture clip that is essentially a closed ring. The term "closed ring" includes a ring having a continuous periphery (for example, FIG. 31a) and also a ring with a discontinuous periphery (for example, FIG. 32a). In the discontinuous periphery ring, the discontinuity or space between ring ends is smaller than the diameter of suture thread. Accordingly, it is unlikely that suture thread will pass through the small opening or discontinuity in the periphery of the ring.

Figure 31A:
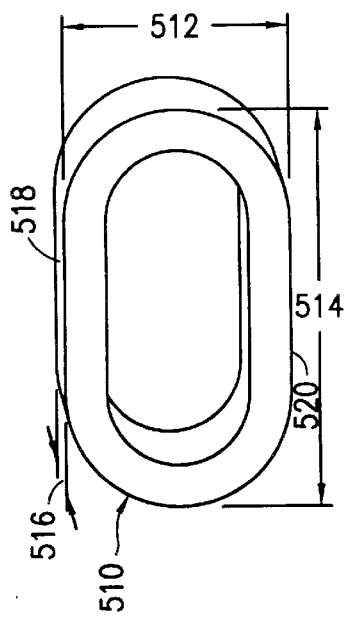
FIGS. 31a, 31b and 31c illustrate a continuous oval or elliptical ring clip.

FIG. 31a shows suture clip 510 formed as an oval or elliptical ring. The ring clip 510 is flattened or deformed on one set of opposing sides. Suture clip 510 has a narrow lateral aspect 512 and a longer longitudinal aspect 514. Ring 510 has a width 516. Appliance jaws 435, 436 act on opposing lateral side outer surfaces 518, 520 which define opposing portions of the laterally narrow aspect 512 of ring 510.

Figure 31B:
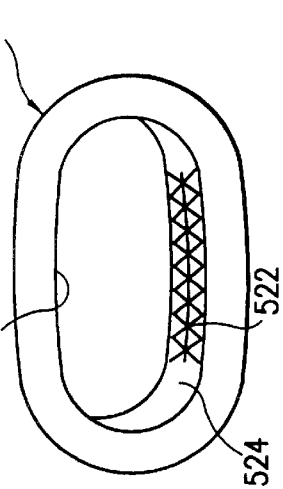

FIG. 31b diagrammatically illustrates ring 510 having a plurality of grooves 522 on an inboard surface 524 of opposing lateral side walls. Inboard surface 526 of the upper lateral wall is also grooved. As explained earlier, the grooves in a preferred embodiment are in an asterisk pattern which, upon closure of the ring (FIG. 31c), enhances the grip of the clip on suture thread.

Figure 31C:
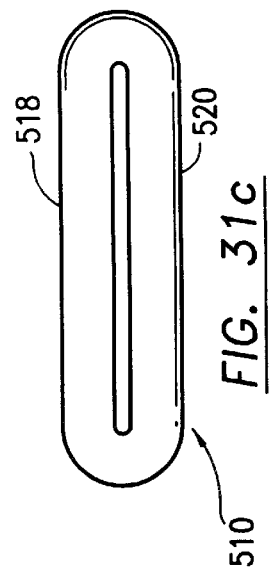

FIG. 31c diagrammatically shows ring 510 in a fully collapsed mode. To achieve fully collapsed mode shown in FIG. 31c, appliance jaws 135, 136 have compressed lateral ring body portions 518, 520 together.

FIG. 31b shows ring 510 having a discontinuous periphery. Specifically, ring 510 is a split ring and has a very small opening 530 on its periphery. Opening 530 is small compared to the diameter of the suture thread. FIG. 31a shows ring 510 and discontinuous feature 530.

FIG. 31a shows oval or elliptical suture ring clip 510 being squared off. As used herein, the term "oval" and "elliptical" includes a squared. off ring body shown in FIG. 33a. In this sense, the ring suture clip is similar to the heart shape suture clip shown in FIG. 8 except hook ends 20, 22 are eliminated and the terminal end faces are juxtaposed substantially adjacent each other such that small discontinuity 530 is smaller than the diameter of the suture thread.

Figure 33B:
FIGS. 33a and 33b illustrate a squared-off oval ring in a full and a collapsed state.
Figure 32A:
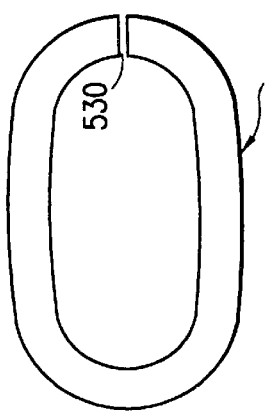
FIGS. 32a and 32b illustrate discontinuous ring clips.

FIG. 33b shows that upon collapse of suture clip 510, the discontinuity 530 closes.

Figure 34:
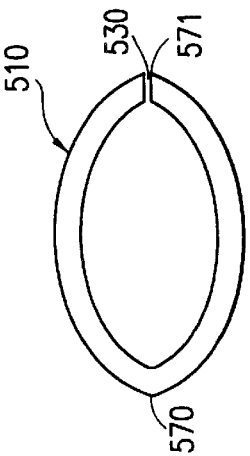
FIG. 34 illustrates a football shaped ring clip.
Figure 32B:
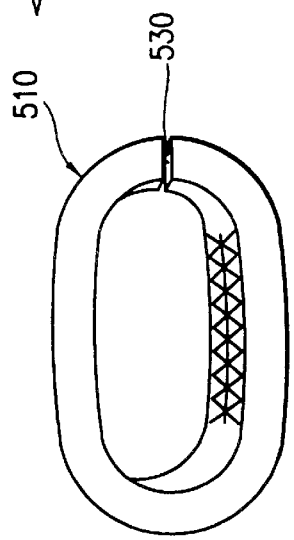
Figure 33A:
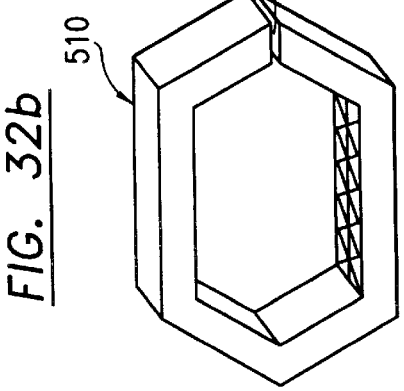

FIG. 34 diagrammatically illustrates a football shaped clip 5 10 which is defined as a ring but the ring includes left and right points or tips 570, 571. In FIG. 34, clip 510 also includes discontinuity 530.

The claims appended hereto are meant to cover modifications and changes within the scope and spirit of the present invention.

What is claimed:

1. A surgical. appliance for clipping together suture thread based upon compressive force applied by a user on movable handle members comprising:
   a suture clip having a pair of plates forming a vertex and substantially defining an acute angle, each plate having a remote terminal edge with an inwardly facing hook, said suture thread passing through a mouth formed by each terminal edge and solid thread captured in an inboard region of said clip;
   a pair of opposing appliance jaws which controllably move toward and away from each other, said jaws having distal end channels which capture said suture clip therein; and,
   an elongated mechanical linkage attached at a proximal end to said compressible handle members and attached at a distal end to said opposing appliance jaws, said linkage transferring compressive handle force of said user to compressive appliance jaw force acting on said suture clip, said mechanical linkage includes an elongated tube with a movable control member extending from said handle to said appliance jaws.

2. A surgical appliance as claimed in claim 1 including a transverse blade to cut said suture.

3. A surgical appliance as claimed in claim 2 wherein said blade is transverse the length of the suture as it passes through said inboard region of said clip.

4. A surgical appliance as claimed in claim 2 wherein said blade is mounted on one of said appliance jaws.

5. A surgical appliance as claimed in claim 1 including a blade mounted on one appliance jaw and an anvil defined on the other appliance jaw, said blade and anvil disposed at an inboard position on said appliance jaw relative to said distal end channels holding said clip.

6. A surgical appliance as claimed in claim 5 wherein said anvil includes a cut-out to trap said suture and blade therein.

7. A surgical appliance for clipping together suture thread based upon compressive force applied by a user on movable handle members comprising:
   a suture clip having a pair of plates forming a vertex and substantially defining an acute angle, each plate having a remote terminal edge with an inwardly facing hook, said suture thread passing through said mouth and captured in an inboard region of said clip;
   a pair of opposing appliance jaws which controllably move toward and away from each other, said jaws having distal end channels which capture said suture clip therein; and,
   an elongated mechanical linkage attached at a proximal end to said compressible handle members and attached at a distal end to said opposing appliance jaws, said linkage transferring compressive handle force of said user to compressive appliance jaw force acting on said suture clip, wherein said mechanical linkage includes a longitudinally movable member having distal actuator surfaces acting on cam control surfaces of said appliance jaws.

8. A surgical appliance for clipping together suture thread based upon compressive force applied by a user on movable handle members comprising:
   a suture clip having a pair of plates forming a vertex and substantially defining an acute angle, each plate having a remote terminal edge with an inwardly facing hook, said suture thread passing through said mouth and captured in an inboard region of said clip;
   a pair of opposing appliance jaws which controllably move toward and away from each other, said jaws having distal end channels which capture said suture clip therein; and,
   an elongated mechanical linkage attached at a proximal end to said compressible handle members and attached at a distal end to said opposing appliance jaws, said linkage transferring compressive handle force of said user to compressive appliance jaw force acting on said suture clip,
   wherein said appliance jaws are pivotally linked together, said appliance jaws having inboard extenders opposite said pivot and clip channels, and said mechanical linkage includes a push actuator linked to appliance jaw extenders.

9. A surgical appliance for clipping together suture thread based upon compressive force applied by a user on movable handle members comprising:
   a suture clip having a pair of plates forming a vertex and substantially defining an acute angle, said plates having remotely extending interleaveable tabs with terminal edges forming an inwardly facing hooks, said hooks define a clip mouth and said suture thread passing through said mouth and captured at an inboard region of said clip;
   a pair of opposing appliance jaws which controllably move toward and away from each other, said jaws having distal end channels which capture said suture clip therein; and, an elongated mechanical linkage attached at a proximal end to said compressible handle members and attached at a distal end to said opposing appliance jaws, said linkage transferring compressive handle force of said user to compressive appliance jaw force acting on said suture clip;
   wherein said appliance jaws are pivotally linked together, said appliance jaws having inboard extenders opposite said pivot and clip channels, and said mechanical linkage includes a push actuator linked to appliance jaw extenders.

10. A surgical appliance as claimed in claim 9 wherein said mechanical linkage includes an elongated tube with a movable control member extending from said handle to said appliance jaws.

11. A surgical appliance as claimed in claim 9 including a transverse blade to cut said suture.

12. A surgical appliance as claimed in claim 11 wherein said blade is transverse the length of the suture as it passes through said inboard region of said clip.

13. A surgical appliance as claimed in claim 11 wherein said blade is mounted on one of said appliance jaws.

14. A surgical appliance as claimed in claim 9 including a blade mounted on one appliance jaw and an anvil defined on the other appliance jaw, said blade and anvil disposed at an inboard position on said one appliance jaw relative to said distal end channels holding said clip.

15. A surgical appliance as claimed in claim 14 wherein said anvil includes a cut-out to trap said suture and blade therein.

16. A surgical appliance for clipping together suture thread based upon compressive force applied by a user on movable handle members comprising:

a suture clip having a pair of plates forming a vertex and substantially defining an acute angle, said plates having remotely extending interleaveable tabs with terminal edges forming an inwardly facing hooks, said hooks define a clip mouth and said suture thread passing through said mouth and captured at an inboard region of said clip;

a pair of opposing appliance jaws which controllably move toward and away from each other, said jaws having distal end channels which capture said suture clip therein; and, an elongated mechanical linkage attached at a proximal end to said compressible handle members and attached at a distal end to said opposing appliance jaws, said linkage transferring compressive handle force of said user to compressive appliance jaw force acting on said suture clip;

wherein said mechanical linkage includes a longitudinally movable member having distal actuator surfaces acting on cam control surfaces of said appliance jaws.

17. A suture clip for attachment of suture thread comprising a ring shaped as one of an oval and an ellipse, said ring having a lumen through which is thread said suture thread, said ring has two, opposing flat surfaces establishing opposing sides of said lumen which are grooved to lock onto said suture thread.

18. A suture clip as claimed in claim 17 wherein said ring is not continuous about its periphery.

19. A suture clip as claimed in claim 17 wherein sad ring has a longitudinal aspect which is longer than a lateral aspect thereby establishing one of said oval and elliptical shape.

20. A suture clip as claimed in claim 17 wherein said grooved opposing surfaces carry grooves forming an asterisk pattern.

21. A method for attachment of elongated suture thread comprising the steps of:

providing a clip shaped as one of an oval ring and an elliptical ring having a lumen, a narrow aspect and a longitudinal aspect normal to said narrow aspect;

capturing said ring and placing said lumen normal to the longitudinal aspect of said suture thread;

passing said suture thread through said lumen;

collapsing said ring over said suture by compressive force applied to a narrow aspect of said ring.

22. A method for attachment of suture thread as claimed in claim 21 including the step of providing a closed loop of elongated wire, passing said closed loop of wire through said lumen of said ring, threading said suture through said closed loop wire, pulling said suture threaded closed wire loop through and out of said ring lumen thereby threading said suture thread through said ring lumen.

23. A surgical appliance for clipping together elongated suture thread based upon compressive force applied by a user on movable handle members comprising:

a suture clip having a ring shaped as one of an oval and an ellipse, said ring having a lumen, said ring having a narrow aspect and a longitudinal aspect;

a closed loop of elongated wire for threading said suture thread through said ring lumen;

a pair of opposing appliance jaws which controllably move towards and away from each other, said jaws having distal end channels which capture said suture clip therein normal to said elongated suture thread; and, an elongated mechanical linkage attached at a proximal end to said compressible handle members and attached at a distal end to said opposing appliance jaws, said linkage transferring compressive handle force of said user to compressive appliance jaw force acting on said suture clip.

24. A surgical appliance as claimed in claim 23 including a transverse blade to cut said suture.

25. A surgical appliance as claimed in claim 23 wherein said closed loop of wire is mounted onto a base and said base is longitudinally movable with respect to said appliance jaws.

26. A surgical appliance as claimed in claim 23 wherein said ring is discontinuous about its periphery.

* * * * *